United States Patent [19]
Kawagoe et al.

[11] Patent Number: 5,714,119
[45] Date of Patent: Feb. 3, 1998

[54] STERILIZER

[75] Inventors: Nobukazu Kawagoe, Toyonaka; Shigeru Oyokota, Takatsuki; Yoshihiro Kiuchi, 1-12-1, Katusuradai, Aoba-Ku, Yokohama-Shi, Kanagawa, 227; Kiyoyuki Takesako, 187-176, Honmokumanzaka, Naka-Ku, Yokohama-Shi, Kanagawa, 231, all of Japan

[73] Assignees: Minolta Co., Ltd., Osaka; Yoshihiro Kiuchi; Kiyoyuki Takesako, both of Yokohama, all of Japan

[21] Appl. No.: 409,657

[22] Filed: Mar. 24, 1995

[30] Foreign Application Priority Data

Mar. 24, 1994 [JP] Japan ................... 6-053787
May 27, 1994 [JP] Japan ................... 6-115234

[51] Int. Cl.[6] ................... A61L 2/00; A61L 9/00
[52] U.S. Cl. ................... 422/21; 422/22; 422/186.29; 422/292; 422/293; 422/307; 422/109
[58] Field of Search ................... 422/1, 21, 22, 422/186, 292, 293, 307, 308, 3, 105, 107, 108, 109, 186.29; 250/455.11

[56] References Cited

U.S. PATENT DOCUMENTS

| | | | |
|---|---|---|---|
| 4,448,750 | 5/1984 | Fuesting | 422/20 |
| 4,774,415 | 9/1988 | Biegel et al. | 250/455.11 |
| 4,875,407 | 10/1989 | Inagaki | 99/451 |
| 5,039,865 | 8/1991 | Koji | 250/455.11 |
| 5,120,499 | 6/1992 | Baron | 422/24 |
| 5,135,721 | 8/1992 | Richard | 422/111 |
| 5,240,675 | 8/1993 | Wilk et al. | 422/22 |
| 5,247,178 | 9/1993 | Ury et al. | 250/455.11 X |

FOREIGN PATENT DOCUMENTS

| | | |
|---|---|---|
| 63-246164 | 10/1988 | Japan. |
| 4-364853 | 12/1992 | Japan. |
| 5-34966 | 5/1993 | Japan. |

*Primary Examiner*—Nina Bhat
*Attorney, Agent, or Firm*—Burns, Doane, Swecker & Mathis, LLP

[57] ABSTRACT

A sterilizer supplies liquid over an object and then irradiates far-infrared radiation to the object. The object is fully sterilized since the supplied liquid well absorb far-infrared radiation with sterilizing effect.

25 Claims, 4 Drawing Sheets

STERILIZER

BACKGROUND OF THE INVENTION

1. Field of the Invention

The present invention relates to a sterilizer for sterilizing floor surfaces, shoe soles, fingers, paper and the like in a simple and effective manner.

2. Description of the Related Art

In the field of conventional sterilizers, devices have been realized wherein when the object of sterilization cannot be heated to high temperature, the object is treated with an application of disinfectant, or irradiated by ultraviolet light to achieve sterilization. Devices have also been made practical wherein, after washing hands, the fingers are irradiated by a relatively weak ultraviolet radiation to achieve some degree of sterilization. Furthermore, long-term heating at high temperature accomplishes sterilization using an autoclave device when the object of sterilization can tolerate heating at high temperature.

Sterilizers using far-infrared radiation such as are disclosed in Japanese Examined Patent Application No. HEI5-34966 and Japanese Unexamined Patent Application No. SHO63-246164. The aforesaid disclosures pertain to techniques for irradiating an object which can readily absorb far-infrared radiation such as foodstuffs and the like with far-infrared radiation, so as to destroy the bacteria adhering to or contained in said object by heating the object itself.

Japanese Unexamined Patent Application No. HEI4-364853 discloses a sterilizer for containers such as bottles, cans and the like. This disclosure pertains to a sterilizer wherein after an optional fluid to prevent heating is adhered to a container or the cover of said container, the fluid and container or cover of said container are heated using a heating means such as a far-infrared lamp, far-infrared heater, optical wavelength collector heating using an infrared lamp, flame plasma, high frequency heating, microwave, focusing a visible light lamp, ultraviolet radiation focusing, laser emission, semiconductor laser, heated air blower, fiber to heat the container or container cover for a short time via vaporization of the fluid while preventing abnormal heating.

Methods have also been proposed wherein a strong acid aqueous oxide produced by electrolysis through a separating membrane of a small amount of an electrolyte (e.g., salt) added to water is used to destroy Staphylococcus aureus. For example, strongly acidic water in the oxidative condition having a pH of 2.7 or less and oxidation-reduction potential of 1050 mV is obtainable using a strong acid solution generating device (Oxilyzer; Miura Denshi K. K.), so as to study the application of strong acid aqueous oxide as a germicide.

The disinfectants used in the aforesaid conventional sterilization methods have certain disadvantages inasmuch as the produce resistant bacteria, and, in the case of floor disinfectants, adverse physiological effects on users due to odor and toxicity. Furthermore, in food preparation facilities there are disadvantages insofar as disinfectants usable for disinfecting equipment and facility are restricted to sodium hypochlorite solution and the like, and the duration of sterilizing effectiveness is reduced by corrosion of metal.

Methods using ultraviolet radiation are disadvantageous insofar as said radiation is harmful to human skin and portions of the object covered by minute debris or detritus may not be sterilized. Manually directed sterilization-drying devices using weak ultraviolet radiation are disadvantageous insofar as they require considerable time for drying even to achieve weak sterilization effect.

In methods of autoclaving which heat at high temperature for a prolonged period, disadvantages arise when sterilizing scalpels, acupuncture/moxibustion needles and the like insofar as such objects are annealed by gradual cooling after heating to a high temperature, thereby making them unusable for their intended purpose.

Methods using far-infrared radiation, such as are described in Japanese Examined Patent Application No. HEI5-34966 and Japanese Unexamined Patent Application No. SHO63-246164, are effective for objects that can be heated to high temperatures, but cannot be used with objects that decompose or burn when heated to high temperature such as floors, human skin and the like.

Furthermore, a device disclosed in Japanese Unexamined Patent Application No. HEI4-364853 sterilizes by heating wherein said heating occurs after a fluid is applied to the object to be sterilized, and the fluid is simply a means to prevent abnormally excessive heating of the object which is heated for a short time. That is, it is believed that this conventional example also does not provide adequate sterilization of an object which cannot be heated to high temperature such as human skin and the like.

Methods which achieve sterilization of Staphylococcus aureus using a strong acid aqueous oxide (strongly acidic water in the oxidative condition) which is readily affected by organic material such as proteins and the like, such that said aqueous oxides react with said organic materials with a resultant reduction in the effectiveness of sterilization. That is, sterilization effectiveness is reduced by the reaction of the water in the oxidative condition with organic material in the dirt at the site at which sterilization is being performed, necessitating the use of the disinfectant as a fluid flow, thereby disadvantageously increasing the amount of disinfectant consumption. A further disadvantage arises in the difficulty of disinfecting a flow and the like using a fluid flow of disinfectant.

SUMMARY OF THE INVENTION

An object of the present invention is to provide a sterilizer and sterilization method capable of sterilizing objects which cannot be heated to high temperatures without using disinfectant or ultraviolet radiation.

These and other objects, advantages and features of the invention will become apparent from the following description thereof taken in conjunction with the accompanying drawings which illustrate specific embodiments of the invention.

BRIEF DESCRIPTION OF THE DRAWINGS

In the following description, like parts are designated by like reference numbers throughout the several drawings.

DETAILED DESCRIPTION OF THE PREFERRED EMBODIMENTS

The preferred embodiments of the present invention are described hereinafter with reference to the accompanying drawings.

In the following embodiments, like parts are designated by like reference numbers.

Figure 1:
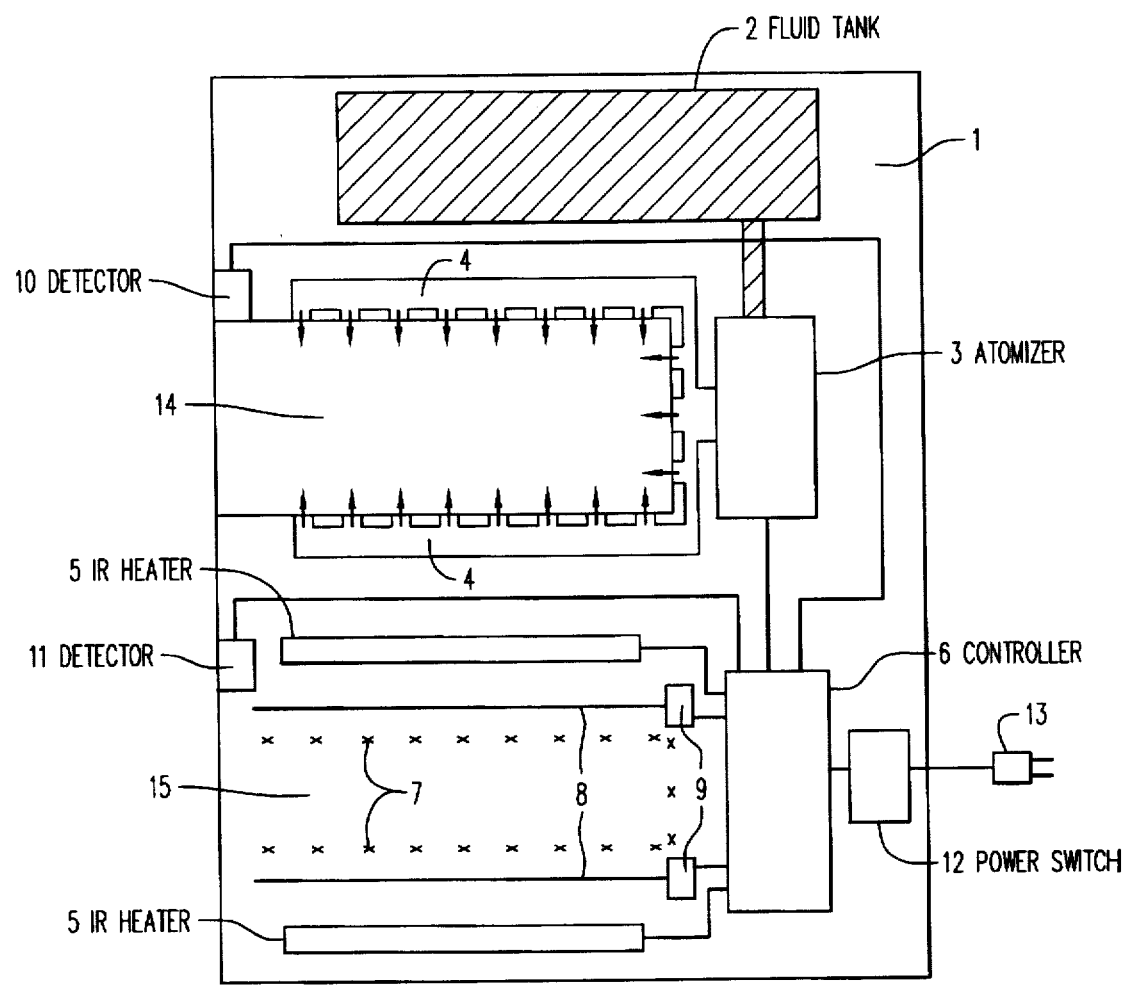
FIG. 1 is a section view of a finger sterilizer of a first embodiment of the present invention.

FIG. 1 is a section view of a finger sterilizer of a first embodiment of the invention.

Reference number 1 refers to the main unit of the finger sterilizer, which is provided with the various components described below.

The main unit of finger sterilizer 1 is provided with first finger insertion unit 14 and second finger insertion unit 15 arranged one above another. First finger insertion unit 14 and second finger insertion unit 15 are apertures provided to allow the insertion of fingers.

Fluid tank 2 is provided in the top section of first finger insertion unit 14. Fluid tank 2 is a tank for accommodating a fluid (e.g., a fluid containing a mix of a small amount of ethanol in water, said fluid being described more fully later) which readily absorbs far-infrared radiation, and is readily spreadable on the surface of an object to be sterilized as it has a weak surface tension.

Reference number 3 refers to an ultrasonic spray section, which is provided behind first finger insertion unit 14. Ultrasonic spray section 3, using a method identical to conventional ultrasonic moistening devices, atomizes the fluid supplied from fluid tank 2 using an ultrasonic oscillator so as to spray said atomizes fluid through spray nozzles 4 provided with a plurality of fine holes at the leading end thereof to spray fingers inserted into first finger insertion unit 14.

Spray nozzles 4 are provided at the top surface, bottom surface, side surfaces, and interior surface of first finger insertion unit 14 so as to uniformly apply the aforesaid fluid on the fingers inserted into first finger insertion unit 14.

Reference number 10 refers to a first finger detection section comprising a photosensor for detecting fingers inserted into first finger insertion unit 14, and is provided near the entrance aperture to said first finger insertion unit 14. Reference number 11 refers to a second finger detection section comprising a photosensor for detecting fingers inserted into second finger insertion unit 15, and is provided near the entrance aperture to said second finger insertion unit 15.

Reference number 5 refers to far-infrared heaters for emitting far-infrared radiation on fingers inserted in second finger insertion unit 15, which are provided at the top and bottom sections of second finger insertion unit 15. Reference number 8 refers to to a shutter for regulating the amount of far-infrared radiation, and which is provided on the interior side of far-infrared heater 5. Shutter 8 is operated by shutter operation section 9. The far-infrared radiation irradiating fingers can be shielded by closing shutter 8.

Reference number 7 refers to a protective metal net for preventing fingers from encroaching too near the far-infrared heaters, and is provided on the interior side of shutter 8. Reference number 6 refers to a control section provided behind second finger insertion unit 15, and which is connected to first finger detection unit 10, second finger detection unit 11, ultrasonic spray section 3, shutter operation section 9, far-infrared heater 5, and power source switch 12. Control section 6 controls the entire finger sterilizer.

Reference number 13 refers to a power source plug socket for electrical power to finger sterilizer 1. Electricity is supplied to finger sterilizer 1 by setting power source switch 12 to the ON position.

The operation of the aforesaid finger sterilizer is described hereinafter.

When power source switch 12 is set to the ON position, far-infrared radiation heater 5 is turned ON. When fingers are inserted into first finger insertion unit 14, first finger detection section 10 detects the presence of said fingers and output is turned ON. When the output of first finger detection section 10 is turned ON, control section 6 operates ultrasonic spray section 3 to spray the previously mentioned fluid on the inserted fingers. When fingers are removed from first finger insertion unit 14, the output of first finger detection section 10 is turned OFF. When the output of first finger detection section 10 is turned OFF, control section 6 stops operation of ultrasonic spray section 3. The aforesaid fingers are uniformly coated by an application of the aforesaid fluid.

When fingers are inserted into second finger insertion unit 15, second finger detection section 11 detects said fingers and detection output is turned ON. When control section 6 changes the output of second finger detection section 11 from OFF to ON, shutter operation section 9 is controlled so as to open shutter 8 and start irradiation of the fingers by far-infrared radiation, and after a predetermined time said shutter 8 is closed to disrupt the emission of far-infrared radiation. The far-infrared radiation is effectively absorbed by the bacteria on the surface of the skin through the aforesaid fluid, thereby destroying said bacteria. When the fingers are removed from second finger insertion unit 15, the output of second finger detection section 11 changes from ON to OFF, and the finger sterilizer returns to its original state when the power source switch was initially turned ON.

Since control of the fluid application and control of far-infrared radiation emission are independent, far-infrared emission can be accomplished without fluid application, such that sterilizing drying via far-infrared radiation may be used after hand washing.

Although control of far-infrared radiation emission is achieved via shutter 8 in the present embodiment, it is to be noted that emission/non-emission control may be accomplished by changing the direction of far-infrared heater 5.

Although a far-infrared radiation heater capable of high far-infrared radiation emission with low power usage is used to emit far-infrared radiation in the present embodiment, the far-infrared radiation heater must normally have power applied thereto inasmuch as more than 5 minutes is required for heating. Thus, when switching between emission and non-emission states, an operation is necessary to change the aforesaid shutter or direction of the far-infrared radiation heater. In contrast, when an infrared lamp (e.g., Twin Tube infrared radiator model (Helius K. K.), Halogen Heater model (Ushio Denki K. K.)) is used, the filament heat capacity is small which allows high-speed switching wherein instant emission/non-emission switching is simply achieved by ON/OFF switching of the power.

Table 1 shows data (i.e., the relationship between fluid application, distance between the far-infrared heater and the object being sterilized, far-infrared radiation emission time, and sterilizing effectiveness) expressing sterilization effectiveness of the present embodiment.

Symbols used in Table 1 are defined as follows: o indicates complete sterilization; α indicates 50% sterilization; X indicates poor sterilization; blank entries indicate no experimental results.

TABLE 1

| Heater/Object distance (cm) | 1 | 2 | 5 | 3 | 5 | 10 |
|---|---|---|---|---|---|---|
| Fluid application | None | None | None | Yes | Yes | Yes |
| Emission time | | | | | | |
| 3 sec | X | X | | o⁻Δ | o⁻Δ | X |
| 5 sec | X | X | | o | o⁻Δ | Δ⁻X |
| 10 sec | X | X | X | | o | Δ |
| 15 sec | | X | | | | |
| 20 sec | o | Δ | | | | o |
| 30 sec | o | Δ | | | | o |

TABLE 2

| Temp (°C.) | 700 | | | 600 | | | 500 | | |
|---|---|---|---|---|---|---|---|---|---|
| Distance (cm) | 3 | 5 | 10 | 3 | 5 | 10 | 3 | 5 | 10 |
| time (sec | | | | | | | | | |
| 3 s | oΔ | oΔ | X | oΔ | Δ | X | X | X | X |
| 5 s | o | oΔ | ΔX | o | oΔ | X | X | X | X |
| 10 s | | o | Δ | o | o | X | Δ | Δ | X |
| 15 s | | o | | | | oΔ | oΔ | Δ | Δ |
| 20 s | | o | | | | | o | o | Δ |

Coliform bacteria were used as the test bacteria, and the surface temperature of the far-infrared radiation heater was 700° C. The fluid used was a mixture of a small amount of ethanol in water, which had a high degree of far-infrared radiation absorption, weak surface tension, and which readily spread over the object surface.

Figure 4A:
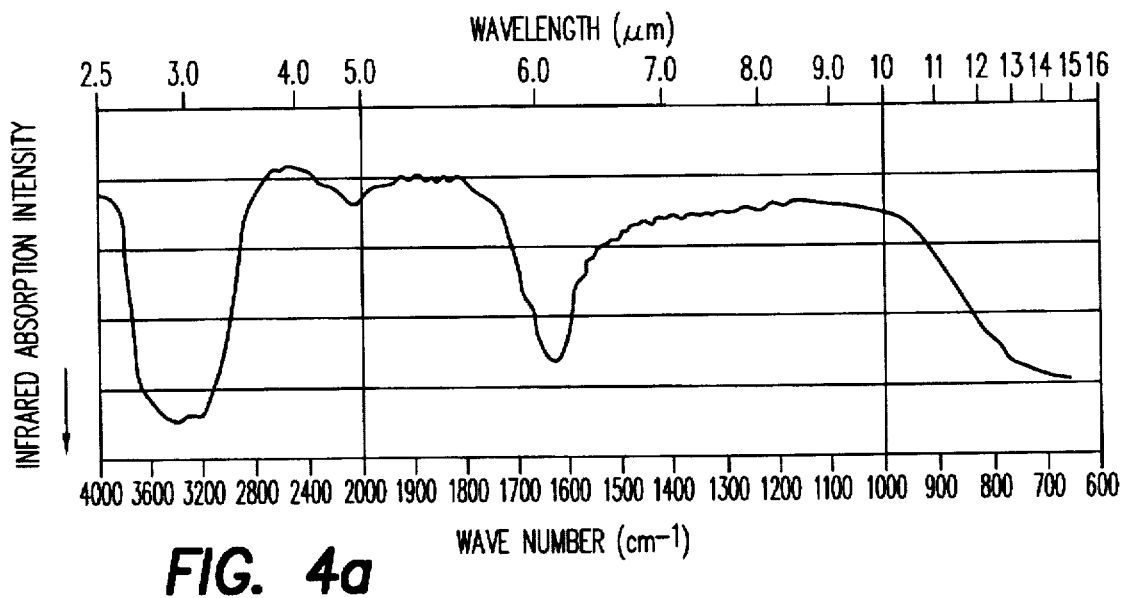
FIG. 4a, 4b are graphs respectively showing the spectral infrared absorption intensity curves of water and ethanol.
Figure 4B:
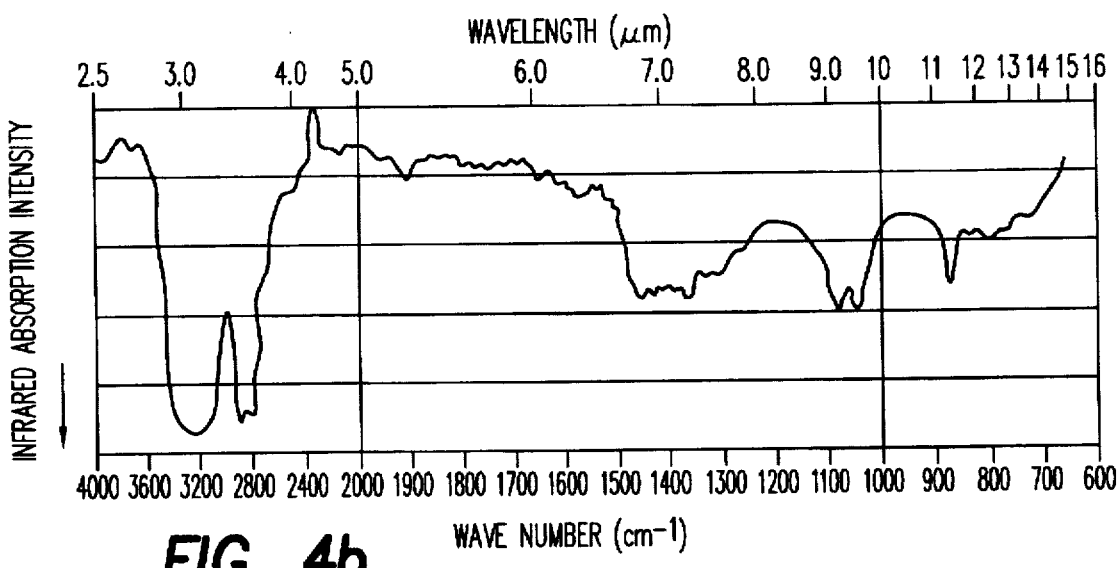

FIG. 4a shows the spectral infrared absorption intensity curve of water, and FIG. 4b shows the spectral infrared absorption intensity curve of ethanol (source: Horiguchi, Sekigai Kyuukou Zusetsu Souran "Illustrated Compendium of Infrared Absorption," pp. 117, Sankyou Shuppan). As can be understood from the illustrations of FIGS. 4a and 4b, the wavelength absorption zone of water is 2.7~3.2 μm and near 6 μm, whereas that of ethanol is 2.9~3.7 μm, such that far-infrared radiation is effectively absorbed within those ranges.

Figure 5:
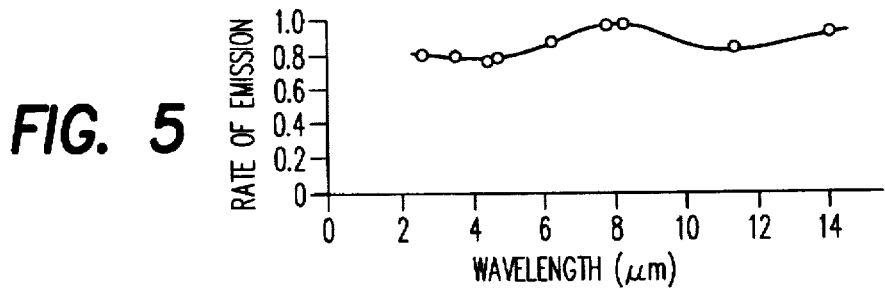
FIG. 5 is a graph showing the emission characteristics of a far-infrared radiation heater.

FIG. 5 shows emission characteristics of a far-infrared radiation heater used in the aforesaid experiments (source: Hachikou Denki Seisakujo catalogue of far-infrared heaters, Catalogue No. 048A). As can be understood from FIG. 5, The aforesaid far-infrared heater used ceramic material as a high efficiency infrared radiator element having high radiation efficiency characteristics across a broad infrared band of 2~14 μm.

As can be understood from Table 1, when the fluid is applied and the distance between the heater and the object being sterilized is 3 cm, adequate sterilization is achieved with irradiation for 5 sec, and when the distance between the heater and object being sterilized is 5 cm, adequate sterilization is achieved with irradiation for 10 sec. Thus, sufficient sterilization is effectively achieved with slight irradiation when fluid is applied compared to non-application of fluid. At this time, sterilization effectiveness is unaffected by vaporization of the fluid, i.e., there is no correlation of sterilization effectiveness relative to complete or incomplete vaporization of the applied fluid.

Although sterilization was effectively achieved without fluid application when the distance between heater and object was 1 cm and irradiation was 20 sec or longer, at such time the object being sterilized attains a high temperature, such that effectiveness is not attributable to direct irradiation by far-infrared radiation, and some of said effectiveness is believed to be due to thermal conduction from the object being sterilized. When the object being sterilized attains high temperature in the aforesaid manner, undesirable decomposition of said object ensues.

Table 2 shows the relationship between the surface temperature of the far-infrared heater and sterilization effectiveness when a fluid is applied. Other conditions and symbols are identical to those described for Table 1.

As can be understood from Table 2, there is slight difference in sterilization effectiveness between far-infrared heater surface temperatures of 600° C. and 700° C., whereas there is a large difference in sterilization effectiveness between 500° C. and 600° C. As can be understood from the graph of spectral radiant existence of a black body shown in FIG. 6, this large deviation is believed to be due to the rapid increase in the amount of infrared radiation in the absorption zone of water, i.e., 2.7~3.2 μm, during the transition from 500° C. to 600° C., as the central wavelength of emitted far-infrared radiation approaches the short wavelength side while the surface temperature of the heater having emission characteristics near the black body increases.

Figure 6:
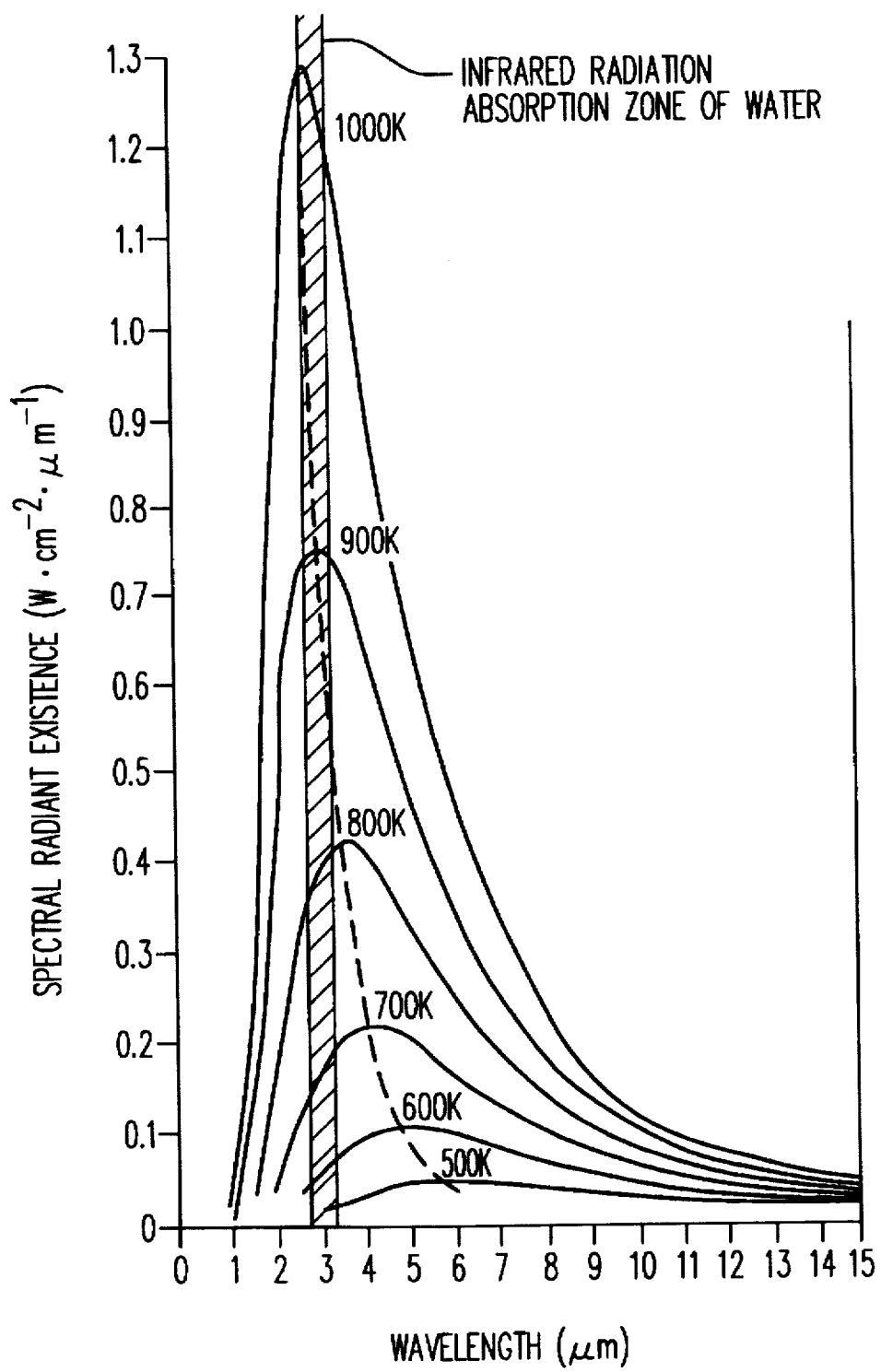
FIG. 6 is a graph showing the spectral radiant existence of a black body.

Although in FIG. 6, the absolute temperature is expressed as T [K], the correlation with Celsius temperature t [C] is as follows: $T_0=273.15K$, $t=T-T_0$.

Water is harmless and inexpensive and is therefore eminently suitable for the fluid used in the present invention. When water is used as the fluid, sterilization effectiveness is markedly improved by maintaining the far-infrared heater surface temperature above 600° C. Although adequate sterilization effectiveness is achieved even when the far-infrared heater surface temperature is 500° C. without fluid application, it is desirable that the far-infrared heater surface temperature be 600° C. or higher when sterilization in a short time is required.

In the first embodiment, the fluid application which readily absorbs far-infrared radiation, has weak surface tension, and readily spreads over the surface of the object being sterilized has been described by way of example using a mixture of a small amount of ethanol in water. A further explanation of the mixture of ethanol in water is presented hereinafter.

Water is a fluid which effectively absorbs far-infrared radiation and has a high absorption rate in a wavelength range of 2.7~3.2 μm. However, the surface tension of water is relatively high at 72.75 dynes/cm² at 20° C., and cannot be uniformly applied due to the performance of the fluid spray device which produces ubiquitous droplets, but the surface tension of the fluid can be mitigated by mixing a small amount of ethanol which has a surface tension of 22.27 dynes/cm². On the other hand, sufficient effectiveness can be achieved using water alone when high uniformity of application characteristics can be achieved by the fluid spray device.

Although tables 1 and 2 show test data using coliform bacteria, staphylococcus bacteria required 1.5 times the emission time of coliform bacteria to achieve sterilization. In the case of fungi, water was not adequately effective, and required 10 times greater emission time.

On the other hand, when an aqueous fluid having a pH of less than 2.7 and oxidation-reduction potential greater than 1050 mV is used instead of water (hereinafter referred to as "aqueous oxide"), markedly increased sterilization effectiveness can be obtained due to the compounded effect of sterilization effectiveness of the aqueous oxide, such that even fungi can be completely eradicated by far-infrared radiation for about 10 seconds after application of aqueous oxide.

Since adequate sterilization effectiveness is not obtained when hydrochloric acid adjusted to a pH of 2.7 is used instead of aqueous oxide, it is believed that oxidation-reduction potential rather than pH is the determinative factor in sterilization effectiveness.

Since aqueous oxide is readily affected by organic materials adequate effectiveness cannot be obtained using a simple application at the scene. However, when an application of aqueous oxide is used in combination with far-infrared radiation, the mutual weak points of sterilization effectiveness supplemented such that sterilization is effective for virtually all bacteria.

Examples of useful aqueous oxides include strong acid aqueous oxide produced by a strong acid solution generating device (Oxilyzer; Miura Denshi K. K.), such as strongly acidic water in the oxidative condition (with extremely high oxidation-reduction potential of 1050 mV or greater).

There are various methods for increasing the oxidation-reduction potential of water such as, for example, adding a small amount of sodium hypochlorite to water. Accordingly, the aqueous oxide is not limited to strongly acidic aqueous oxides, insofar as water or aqueous solution having a high oxidation-reduction potential may be used.

Furthermore, oxides of mineral water extracted from vermiculite, an aerated mica, may be used. Such oxides of mineral water are effective for sterilization because they include various types of minerals and strong oxidizing action.

Figure 2:
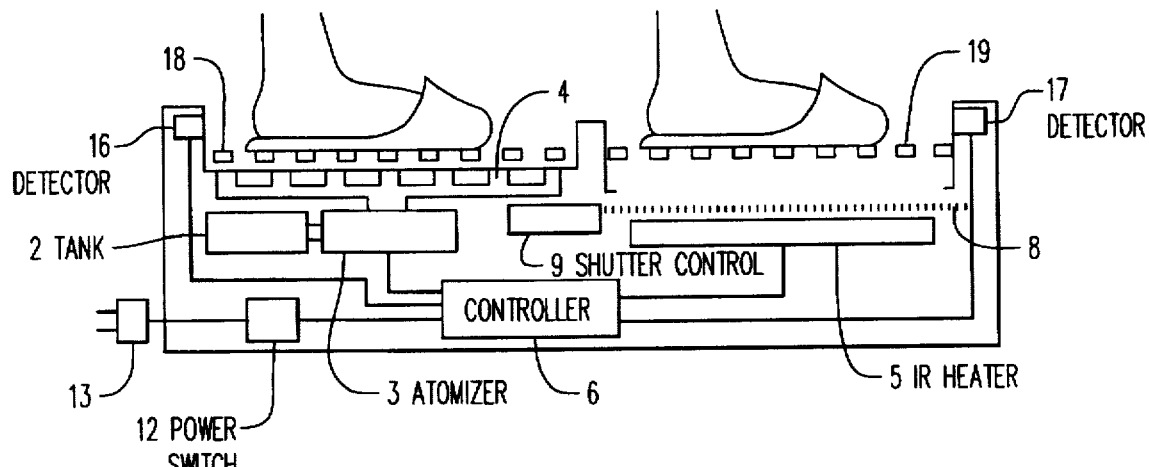
FIG. 2 is a section view of a sterilizer for the bottom of footwear of a second embodiment of the invention.

The sterilizer for the soles of footwear (slippers and the like) of a second embodiment of the invention is described hereinafter with reference to FIG. 2. Elements having similar function to those described in the first embodiment are omitted from the following description.

This sterilizer comprises a fluid application section and, disposed anteriorly thereto, a far-infrared irradiation section.

The fluid application section comprises first protective metal net 18 for accommodating feet, spray nozzles 4 disposed below said first protective metal net 18, first foot detector 16 disposed at the side of said first protective metal net 18, ultrasonic spray section 3 disposed below said spray nozzles 4, and fluid tank 2 disposed horizontally to ultrasonic spray section 3. Spray nozzles 4 are provided with a plurality of small holes, and a plurality of said nozzles are individually arrayed so as to be capable of uniformly applying a fluid on the sole of a foot (shoe). First foot detector 16 detects a foot wearing a show placed on first protective metal net 18 on the top of spray nozzles 4.

The far-infrared irradiation section comprises second protective metal net 19 for accommodating feet, shutter 8 disposed below second protective metal net 19, far-infrared radiation heater 5 disposed below shutter 8, second foot detector 17 disposed at the side of second protective metal net 19, and shutter operating section 9 disposed at the side of shutter 8. Second foot detector 17 detects a foot wearing a show placed on second protective metal net 19 on the top of far-infrared radiation heater 5.

Control section 6 is provided in the bottom section of the sterilizer, and is connected to first foot detector 16, second foot detector 17, ultrasonic spray section 3, shutter operating section 9, far-infrared radiation heater 5, and power source switch 12. Control section 6 controls the entire sterilizer.

The operation of the sterilizer follows hereinafter.

When power source switch 12 is set to the ON position, far-infrared radiation heater 5 is turned ON. When a foot is placed on first protective metal net 18, it is detected by first foot detector 16 and said detector output is turned ON. When first foot detector output is turned ON, control section 6 operates ultrasonic spray section 3 to spray a fluid on the shoe sole. When the foot is removed from the top of first protective metal net 18, the output of first foot detector 16 is turned OFF. When the output of first foot detector 16 is turned OFF, control section 6 stops the operation of ultrasonic spray section 3. A uniform application of fluid is applied to the sole of the shoe by the aforesaid process.

When a foot is placed on second protective metal net 19, second foot detector 17 detects its presence and output of the detector is turned ON. When the output of second foot detector 17 changes from OFF to ON, control section 6 determines whether or not a constant time has elapsed after fluid application. If a constant time has not elapsed, shutter operating section 9 is controlled to open shutter 8, far-infrared radiation is emitted to the sole of the shoe, and shutter 8 is then closed after a predetermined time to interrupt said far-infrared radiation emission.

Far-infrared radiation is effectively absorbed by the bacteria on the shoe sole through the aforesaid fluid, thereby destroying the bacteria. When the foot is removed from second protective metal net 19, the output of second foot detector 17 is turned OFF, and the sterilizer returns to the state when power source switch 12 was initially turned ON.

In the present embodiment, far-infrared radiation emission is controlled by control section 6 so as to not function within a constant time after fluid application, thus avoiding erroneous irradiation of a shoe sole which has not had a fluid application, and assuring reliable sterilization.

Although far-infrared radiation emission is controlled by shutter 8 in the present embodiment, emission/non-emission control may also be accomplished by changing the direction of far-infrared radiation heater 5. Furthermore, emission/non-emission may also be controlled by ON/OFF switching of the power to a halogen infrared lamp instead of a far-infrared radiation heater.

Figure 3:
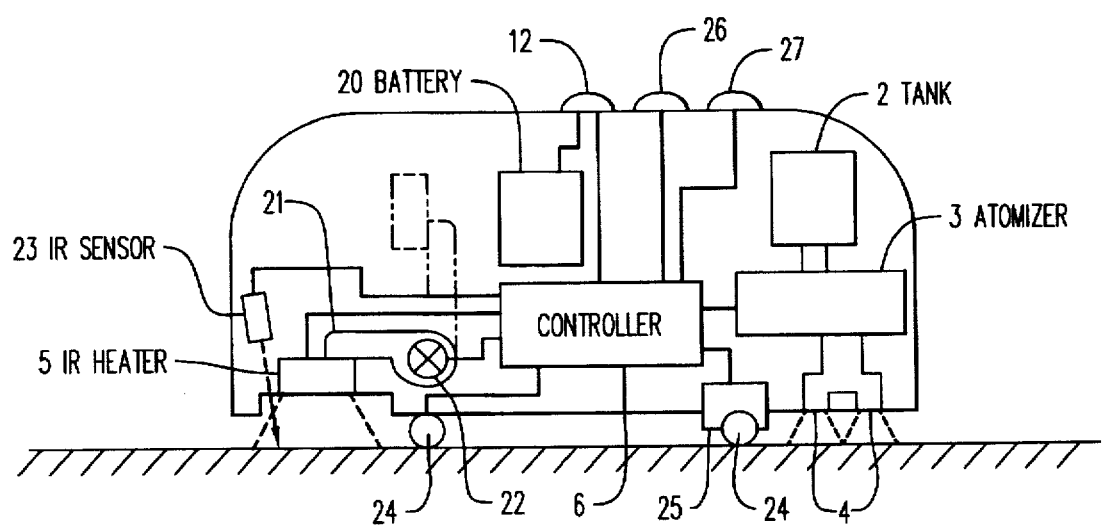
FIG. 3 is a section view of a floor surface sterilizer of a third embodiment of the invention.

The floor surface sterilizer of a third embodiment of the invention is described hereinafter with reference to FIG. 3. Elements having functions similar to those described in the first embodiment are omitted from the following description.

This sterilizer is provided with a drive wheels 24 at the bottom of the main unit, so as to be capable of running on the floor surface. Furthermore, the sterilizer normally travels to the right in FIG. 3 (hereinafter the right side of FIG. 3 shall be referred to as "front").

Spray nozzles 4 having a plurality of small holes formed at the leading end thereof are provided at the front portion of the sterilizer, so as to spray fluid on the floor surface. An ultrasonic spray section 3 is provided above spray nozzles 4, and a fluid tank 2 is provided above said spray section 3.

Far-infrared radiation heater 5 is provided at the bottom rear portion of the sterilizer, so as to irradiate the floor surface with far-infrared radiation. Far-infrared radiation heater 5 is supported by heater support member 21 attached to the top of said heater 5. Heater support member 21 is connected to heater drive section 22, such that far-infrared radiation heater 5 is rotatably driven with heater support member 21 in accordance with the operation of heater drive section 22. Far-infrared radiation heater 5 attains two positions, i.e., a floor irradiation position and floor non-irradiation position (indicated by the dashed line in the drawing) via the aforesaid drive section.

Infrared temperature sensor 23 is provided near far-infrared radiation heater 5 to measure the temperature of the floor surface. Drive speed measuring section 25 is connected to drive wheels 24 to measure the drive speed by detecting the rotation of drive wheels 24.

Power source switch 12, start switch 26, and stop switch 27 are provided on the top portion of the sterilizer.

Provided centrally within the sterilizer are battery 20 and control section 6. Control section 6 is connected to drive wheels 24, drive speed measuring section 25, ultrasonic spray section 3, far-infrared radiation heater 5, heater drive section 22, infrared temperature sensor 23, power switch 12, start switch 26, and stop switch 27. Control section 6 controls the entire sterilizer.

The operation of the sterilizer is described hereinafter.

The initial state has far-infrared radiation heater 5 set at the non-irradiation position. When power source switch 12 is turned ON, power is supplied to far-infrared radiation heater 5 and said heater 5 is heated. After far-infrared radiation heater 5 is sufficiently heated and start switch 26 is depressed, control section 6 initiates forward movement at constant speed based on the output from drive speed measuring section 25, such that the sterilizer starts to move on the floor. In FIG. 3, the spray nozzles 4 are provided in front of the wheels. Control section 6 simultaneously starts the operation of ultrasonic spray section 3 and starts spraying of the fluid on the floor.

Control section 6 calculates the driving distance from the start of fluid spraying by adding the drive speed data output from drive speed measuring section 25. When the calculated driving distance is equal to the distance between spray nozzle 4 and the irradiation position of heater 5, i.e., at the moment the irradiation position of heater 5 reaches the position to start spraying, far-infrared radiation heater 5 is moved to the irradiation position by heater drive section 22, and far-infrared irradiation of the floor surface starts.

Only the floor surface to which fluid has been applied is thus irradiated by far-infrared radiation via the aforesaid process. When the previously described process is not adhered to, the floor surface is directly irradiated by far-infrared radiation without fluid application, such that the floor surface is excessively heated beyond necessity and sterilization is not effectively achieved. The previously described process effectively prevents this disadvantage.

Thereafter, the sterilizer drives across the floor at constant speed leaving a uniform fluid application on the floor therebehind which is irradiated by a predetermined amount of far-infrared radiation to achieve excellent sterilization of the floor surface. When drive wheels 24 stops due to the sterilizer confronting an object while driving, the stopping of the drive wheels 24 is detected by drive speed measuring section 25, and heater drive section 22 is operated by control section 6 to move far-infrared radiation heater 5 to the non-irradiation position. Thus, far-infrared irradiation is stopped while driving is stopped, so as to prevent over heating of the floor surface.

When the friction coefficient between drive wheels 24 the floor surface is low so as to cause slipping of said drive wheels 24, drive wheels 24 are rotated even when movement has stopped and drive speed measuring section 25 cannot detect the drive stoppage, such that far-infrared irradiation continues on the same floor surface location and the floor surface starts to over heat. In this instance, abnormal heating of the floor surface is detected at an early stage, via infrared temperature sensor 23. Also, heater drive section 22 is started by control section 6 to move far-infrared radiation heater 5 to the non-irradiation position, thereby preventing over heating of the floor surface and preventing decomposition of the floor.

When stop switch 27 is depressed, ultrasonic spray section 3 stops operation, heater drive section 22 is operated, far-infrared radiation heater 5 is moved to the non-irradiation position, and driving stops.

Although control of irradiation/non-irradiation accomplished by changing the direction of far-infrared radiation heater 5 in the present embodiment, a shutter may also be used as described in the first and second embodiments. Furthermore, control of irradiation/non-irradiation may also be accomplished by ON/OFF switching of power to a halogen infrared lamp instead of the aforesaid far-infrared radiation heater.

In the present embodiment, starting and stopping of the drive and starting and stopping of sterilization is accomplished by the same start switch and stop switch, but it is to be understood that drive and sterilization may be switched independently so as to allow driving only without sterilization. Such an arrangement can be convenient for moving the sterilizer. In such circumstances, the sterilization start switch may be rendered effective only while driving.

Although a device for measuring the temperature of the object being sterilized (fingers, shoe soles and the like) was not provided in the first and second embodiments, when a device is provided for measuring the temperature of the object being sterilized as in the third embodiment and said object is heated above a predetermined temperature, far-infrared irradiation may be stopped so as to prevent burning of the fingers and decomposition of shoes.

The fluid used is not limited to aqueous oxide, water, or mixture of a small amount of ethanol in water, and insofar as the object being sterilized (fingers, shoe soles, floor surface) invaded or ignited, other fluids may be used including fluids having high degrees of far-infrared radiation absorption such as normal propyl alcohol dilution.

Although an ultrasonic spray device was used for fluid application in all the aforesaid embodiments, a centrifugal atomizer may be used to adhere fluid on the object being sterilized more effectively.

Methods using the aforesaid centrifugal atomizer are described below.

Air can be spirally passed through a processing tank accommodating a fluid in a spray state achieved by a centrifugal atomizer, such that dirt and bacteria within the air are adhered to said fluid and thereby eliminated, producing pure air containing large amounts of minute fluid particles. The air containing said fluid particles makes contact with the object being sterilized such that the fluid is effectively adhered thereto.

Furthermore, the fluid may be simply applied to the object being sterilized without using a spray device for fluid application.

In all of the previously described embodiments, a fan may be provided to accelerate drying of the object wetted by the fluid application, and to expel water vapor between far-infrared irradiation portion and the object being sterilized to the outside of the apparatus. Furthermore, when used in a clean room, an HEPA filter may be provided on the fan exhaust port so that minute particles are not discharged outside the apparatus.

As previously described, the present invention applies a fluid which readily absorbs far-infrared radiation on an object to be sterilized prior to irradiation by said far-infrared radiation, and thereafter achieves excellent sterilization without heating said object to high temperature by irradiation via far-infrared radiation over a short period.

Furthermore, sterilization of equipment and installations at food processing sites can be accomplished by far-infrared radiation without using disinfectants, thereby achieving effective sterilization without contamination of foods by said disinfectants, or causing corrosion of metals. Sterilization is also effectively accomplished without changing the flavor of foodstuffs.

Sterilization of metal materials such as scalpels, acupuncture/moxibustion needles and the like may be achieved without heating to high temperatures, thereby preventing deterioration of elasticity and sharpness due to annealing as occurs by conventional methods.

When applying the aforesaid fluid on an object to be sterilized by spraying using an ultrasonic oscillator, it is possible to achieve an extremely uniform application of the fluid on said object.

Furthermore, the far-infrared radiation state may be variable, and a temperature detection device may be provided for the object being sterilized so as to stop far-infrared irradiation when an object is heated above a predetermined temperature, thereby assuring safe sterilization of an object by preventing burning of fingers, and decomposition footwear and the like by heat.

In addition, the sterilizer may be provided with a drive section for self advancement, such that when the drive speed is detected by the drive speed detection section and said speed is controlled to achieve uniform speed, uniform application of fluid on the entire area of the object and uniform irradiation by far-infrared radiation can be automatically achieved.

The far-infrared irradiation state may be variable, and a device may be provided to detect the temperature of the object being sterilized so as to stop far-infrared irradiation of an object when the drive speed detection section detects that driving has stopped. When the aforesaid detection device detects that the temperature of the object being sterilized has exceeded a predetermined temperature and far-infrared irradiation of the object is stopped, thereby avoiding decomposition of a floor surface due to overheating of said floor surface.

In a device wherein a fluid application section is provided anteriorly to a far-infrared radiation section relative to the drive direction, if far-infrared irradiation state transitions form the non-irradiation state to the irradiation state when the irradiation position reaches the fluid application start position, only the floor surface coated by said fluid is irradiated by far-infrared radiation, thereby accurately sterilizing the floor surface.

Although the present invention has been fully described by way of examples with reference to the accompanying drawings, it is to be noted that various changes and modifications will be apparent to those skilled in the art. Therefore, unless otherwise such changes and modifications depart from the scope of the present invention, they should be construed as being included therein.

What is claimed is:

1. A method for sterilizing an object, comprising the steps of:

supplying liquid over an object to be sterilized, said liquid containing a material which functions to sterilize the object and having a far-infrared absorbing attribute to thereby assist the sterilization capability of far-infrared radiation;

emitting far-infrared radiation toward the object after supplying the liquid, said far-infrared radiation itself having sterilization capability; and controlling the emission of radiation such that a temperature of the object does not exceed a predetermined value.

2. A method as claimed in claim 1, further comprising the steps of:

measuring a temperature of the object; and wherein the controlling step stops the emission of radiation when the object temperature exceeds the predetermined value.

3. A method as claimed in claim 1, wherein the supplying step includes the following steps:

atomizing the liquid; and spraying the atomized liquid on the object.

4. A sterilizer for an object independent of the sterilizer itself, comprising:

a movable housing;

an emitter on said housing which emits far-infrared radiation toward an object to be sterilized, said far-infrared radiation itself having sterilization capability;

a liquid supply on said housing which supplies liquid over the object, said liquid being capable of absorbing far-infrared radiation to thereby assist the sterilization capability of the far-infrared radiation; and a controller which controls the emitter so that a temperature of the object does not exceed a predetermined value.

5. A sterilizer as claimed in claim 4, wherein the emitter has an irradiating state and a non-irradiating state, and further comprising:

a selector which selects one state of the emitter from the irradiating state and the non-irradiating state in dependence on a state of movement of the sterilizer.

6. A sterilizer as claimed in claim 5, wherein the selector selects the non-irradiating state when the sterilizer stops movement.

7. A sterilizer as claimed in claim 4, further comprising:

a detector which detects a position of the emitter on a moving path;

and wherein the emitter is arranged on said housing behind the liquid supply with respect to a direction of movement of the sterilizer, and the emitter starts emitting the far-infrared radiation when the detector detects that the emitter reaches a position where the liquid supply starts supplying the liquid.

8. A sterilizer as claimed in claim 4, further comprising:

a thermometer which measures a temperature of the object; and wherein the controller stops the emitter from emitting the far-infrared radiation when the object temperature exceeds the predetermined value.

9. A sterilizer as claimed in claim 4, wherein the liquid supply includes means for atomizing the liquid and spraying the atomized liquid onto the object.

10. A sterilizer as claimed in claim 9, wherein the atomizing means is an ultrasonic oscillator.

11. A sterilizer as claimed in claim 9, wherein the atomizing means is a centrifugal atomizer.

12. A sterilizer as claimed in claim 4, further comprising means for moving the housing.

13. A sterilizer for an object independent of the sterilizer itself, comprising;

a housing;

an emitter on said housing which emits far-infrared radiation toward an object to be sterilized, said far-infrared radiation itself having sterilization capability;

a liquid supply on said housing which supplies over the object, wherein the liquid is a mixture of water and ethanol, and is capable of absorbing far-infrared radiation to thereby assist the sterilization capability of the far-infrared radiation; and a controller which controls the emitter so that a temperature of the object does not exceed a predetermined value.

14. A sterilizer for an object independent of the sterilizer itself, comprising;

a housing;

an emitter on said housing which emits far-infrared radiation toward an object to be sterilized, said far-infrared radiation itself having sterilization capability;

a liquid supply on said housing which supplies liquid over the object, wherein the liquid contains a material which functions to sterilize the object and is capable of absorbing far-infrared radiation to thereby assist the sterilization capability of the far-infrared radiation; and a controller which controls the emitter so that a temperature of the object does not exceed a predetermined value.

15. A sterilizer as claimed in claim 14, wherein the liquid has a pH which is lower than 2.7 and an oxidation-reduction potential which is higher than 1050 mV.

16. A sterilizer as claimed in claim 14, wherein the liquid is solution of sodium hypochlorite.

17. A sterilizer for an object, comprising:

an emitter which irradiates far-infrared radiation toward an object for sterilization; and a moving device by which the entire sterilizer is automatically transported along the object.

18. A sterilizer as claimed in claim 17, wherein the emitter has an irradiating state and a non-irradiating state, and further comprising:

a selector which selects one state of the emitter from the irradiating state and the non-irradiating state in dependence on a state of movement of the sterilizer.

19. A sterilizer as claimed in claim 18, wherein the selector selects the non-irradiating state when the sterilizer stops moving.

20. A sterilizer as claimed in claim 17, further comprising:

a thermometer which measures a temperature of the object; and a controller which stops the far-infrared radiation from the emitter when the object temperature exceeds a predetermined value.

21. A sterilizer for an object independent of the sterilizer itself, comprising:

a movable housing;

an emitter on said housing which emits far-infrared radiation toward an object to be sterilized;

a liquid supply on said housing which supplies liquid over the object; and a controller which controls the emitter such that a temperature of the object does not exceed a predetermined value.

22. A sterilizer for an object independent of the sterilizer itself, comprising:

a first chamber in which the object to be sterilized is inserted;

an emitter on said first chamber which emits far-infrared radiation toward an object inserted in said first chamber;

a second chamber in which the object is inserted; and a liquid supply on said second chamber which supplies liquid over an object inserted in said second chamber.

23. The sterilizer of claim 22, further including a first detector associated with said first chamber for detecting the insertion of an object in said first chamber and activating said emitter to emit radiation, and a second detector associated with said second chamber for detecting the insertion of an object in said second chamber and activating said liquid supply to supply liquid.

24. A sterilizer for an object independent of the sterilizer itself, comprising:

a chamber in which the object is inserted when the object is to be sterilized;

an emitter on said chamber which emits far-infrared radiation toward an object to be sterilized from a plurality of directions of the chamber; and a liquid supply on said chamber which supplies liquid over the object from a plurality of directions of the chamber.

25. The sterilizer of claim 24, further including a detector for detecting the insertion of an object in said chamber and activating said emitter and said liquid supply.

\* \* \* \* \*

UNITED STATES PATENT AND TRADEMARK OFFICE
CERTIFICATE OF CORRECTION

PATENT NO. : 5,714,119
DATED : February 3, 1998
INVENTOR(S) : Nobukazu KAWAGOE, et al.

It is certified that error appears in the above-indentified patent and that said Letters Patent is hereby corrected as shown below:

Title page, item
[30]  Foreign Application Priority Data  should read --
May 27, 1994    [JP]   Japan ....................... 6-115324

Signed and Sealed this

Twenty-second Day of September, 1998

Attest:

BRUCE LEHMAN

*Attesting Officer*     *Commissioner of Patents and Trademarks*